United States Patent [19]

Achiwa

[11] Patent Number: 4,879,389

[45] Date of Patent: Nov. 7, 1989

[54] CHIRAL PHOSPHINOPYRROLIDINE COMPOUNDS AND THEIR USE FOR ASYMMETRIC SYNTHESIS OF OPTICALLY ACTIVE COMPOUNDS

[76] Inventor: Kazuo Achiwa, 11-17, Kamiashiarai 2-chome, Shizuoka-shi, Shizuoka-ken, Japan

[21] Appl. No.: 66,251

[22] Filed: Jun. 25, 1987

[30] Foreign Application Priority Data

Jun. 25, 1986 [JP] Japan ............................. 61-147167
Mar. 9, 1987 [JP] Japan ............................. 62-52177
Mar. 9, 1987 [JP] Japan ............................. 62-52178

[51] Int. Cl.$^4$ .................. C07F 9/65; C07F 7/18; C07B 53/00; B01J 31/02
[52] U.S. Cl. .................. 548/412; 548/406; 548/542; 549/319; 568/814; 568/881; 544/232; 544/243; 544/337; 546/21
[58] Field of Search .................. 548/412; 546/21; 544/337

[56] References Cited

U.S. PATENT DOCUMENTS 4,343,741 8/1982 Townsend ..................... 548/412
4,539,411 9/1985 Brozer et al. .................. 548/412

OTHER PUBLICATIONS

Beck et al., Chem. Abs 103, 215570s (1985).

*Primary Examiner*—Mark L. Berch
*Attorney, Agent, or Firm*—Birch, Stewart, Kolasch & Birch

[57] ABSTRACT

New chiral phosphinopyrrolidine compounds of the general formula:

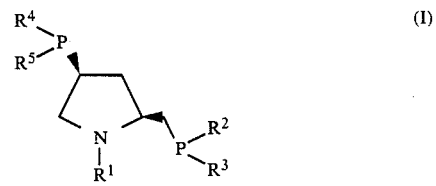

or

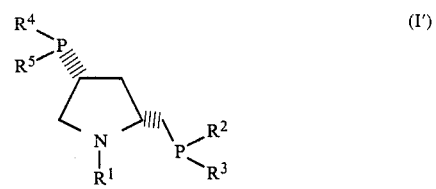

wherein $R^1$ is a hydrogen atom, —COR, —COOR, —CONHR or —SO$_2$—R where R is an alkyl or aryl group, $R^2$ and $R^3$ each represents independently an aryl group which may have a substituent or substituents, and $R^4$ and $R^5$ each represents independently an aliphatic or cycloaliphatic hydrocarbyl group which may have a substituent or substituents, as well as the use of these compounds as ligand for a metal complex catalyst for asymmetric synthesis of optically active compounds. The new chiral phosphinopyrrolidine compounds are useful ligands which attain both of high optical yield and high reaction efficiency in catalytic asymmetric reduction.

6 Claims, No Drawings

CHIRAL PHOSPHINOPYRROLIDINE COMPOUNDS AND THEIR USE FOR ASYMMETRIC SYNTHESIS OF OPTICALLY ACTIVE COMPOUNDS

BACKGROUND OF THE INVENTION

1. Field of the Invention

The present invention relates to new chiral phosphinopyrrolidine compounds and to the use of these compounds as a ligand for a metal complex compound utilizable as a catalyst for asymmetric synthesis. More particularly, the present invention relates to new chiral 2,4-diphosphinopyrrolidine compounds and to the use of these compounds as a ligand for a metal complex compound utilizable as a catalyst for a process for the asymmetric synthesis of optically active compounds by catalytic asymmetric hydrogenation of reducible compounds.

2. Description of the Prior Art

From the past, a number of researches have been made in the field of synthetic chemistry on asymmetric reducing reaction capable of synthesizing optically active compounds directly from optically inactive reducible compounds. In one of the researches, various bis-phosphine ligands have been synthesized and an asymmetric reducing reaction of a reducible compound has been tested using various combinations of such ligands with a transition metal compound as catalyst. In such asymmetric reducing reaction, an optical yield (asymmetric yield) of the product and a reaction efficiency in the reaction are taken up as important factors to evaluate whether the ligand is advantageously utilizable for such reaction or not. The optical yield is the simplest way for knowing whether the ligand is effective for preparing optically active products or not. With respect to the reaction rate, a larger amount of the ligand becomes necessary in case the reaction rate is low. As a means for knowing such relation between the amount of the ligand and the reaction rate, the reaction efficiency is defined by a ratio of the substrate to the ligand in terms of molar ratio. In such asymmetric reducing reactions, however, there is not as yet found such a ligand as satisfies both of the optical yield and the reaction efficiency at the same time (B. Bosnich, "Asymmetric Catalysis" published by Martinus Nijhoff Publishers, Boston, 1986, pp. 19–31).

Under such circumstances, there is a great demand in the field of asymmetric reducing reactions for developing a new ligand which satisfies not only the optical yield but also the reaction efficiency when used as a catalyst with a metal complex for asymmetric reducing reaction of reducible compounds.

BRIEF SUMMARY OF THE INVENTION

Accordingly, it is an object of the present invention to provide new chiral 2,4-diphosphinopyrrolidine compounds useful as a ligand for catalytic asymmetric hydrogenation.

It is another object of the present invention to provide the use of the 2,4-diphosphinopyrrolidine compounds as ligands in catalysts for asymmetric hydrogenation.

It is still another object of the present invention to provide a process for the asymmetric synthesis of optically active compounds by asymmetric hydrogenation of keto or unsaturated compounds.

It is further object of the present invention to provide a technically advantageous process for preparing D-pantolactone from ketopantolactone.

Other and further objects, features and advantages of the present invention will become apparent more fully from the following description.

As a result of extensive researches made for developing new compounds useful as ligands which can afford a satisfactory optical yield and a reaction efficiency in asymmetric synthesis of optically active compounds, it has now been found that new 2,4-diphosphinopyrrolidine compounds are useful as ligands which show high levels of optical yield and reaction efficiency when used together with a transition metal compounds as catalyst for asymmetric hydrogenation of reducible compounds.

In accordance with one embodiment of the present invention, there is provided new chiral phosphinopyrrolidine compounds of the general formula:

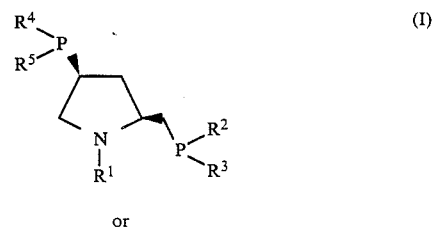

(I)

or

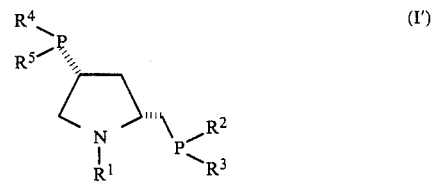

(I')

wherein $R^1$ is a hydrogen atom, —COR, —COOR, —CONHR or —SO$_2$—R where R is an alkyl or aryl group, $R^2$ and $R^3$ each represents independently an aryl group which may have a substituent or substituents, and $R^4$ and $R^5$ each represents independently an aliphatic or cycloaliphatic hydrocarbyl group which may have a substituent or substituents.

In accordance with another embodiment of the present invention, there is provided the use of new chiral phosphinopyrrolidine compounds of the general formula:

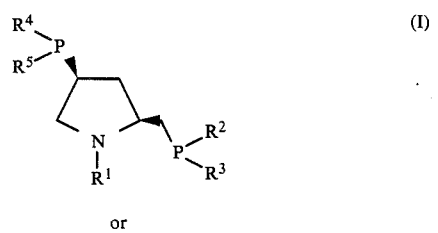

(I)

or

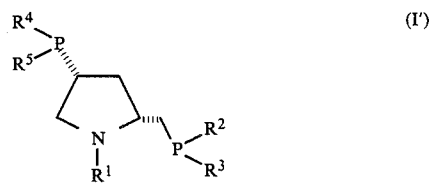

(I')

wherein $R^1$ is a hydrogen atom, —COR, —COOR, —CONHR or —$SO_2$—R where R is an alkyl or aryl group, $R^2$ and $R^3$ each represents independently an aryl group which may have a substituent or substituents, and $R^4$ and $R^5$ each represents independently an aliphatic or cycloaliphatic hydrocarbyl group which may have a substituent or substituents as a ligand for a metal complex compound utilizable as a catalyst for a process for the asymmetric synthesis of compounds having asymmetric carbon atoms by catalytic hydrogenation of a reducible compound having a carbon-to-carbon double bond, carbon-to-nitrogen double bond and/or carbon-to-oxygen double bond in the molecular structure thereof.

The new compounds and their use as ligands for asymmetric synthesis have various features as compared with similar ligands and their use for asymmetric synthesis in the prior arts. The new phosphinopyrrolidine compounds of this invention were developed on the basis of a quite new technical concept found during the present inventor's researches and constitute excellent ligands for asymmetric hydrogenation reactions. Thus, the new phosphinopyrrolidine compounds of this invention attain satisfactorily high levels of optical yield and reaction efficiency at the same time in asymmetric hydrogenation.

DETAILED DESCRIPTION OF THE INVENTION

As a result of the present inventor's extensive researches made on the reaction mechanism of ligands of phosphine series, it has been manifested that a moiety capable of increasing an optical yield of the product and a moiety capable of enhancing the reaction efficiency exist in the molecular structure of the ligands. More particularly, it has been made clear by a result of the present inventor's study that the phosphinopyrrolidine compound of the general formula (I) or (I') possessing especially remarkable properties as a ligand contains a phosphine grouping of the formula:

which gives influence on the increase of the optical yield and aphosphino grouping of the formula:

which gives influence on the enhancement of the reaction efficiency. It has also been found that when $R^2$ and $R^3$ each represents independently an aryl group and concurrently $R^4$ and $R^5$ each represents independently an aliphatic or cycloaliphatic hydrocarbyl group, an optimum result which satisfies both the optical yield and the reaction efficiency can be obtained.

Now discussion is made on the reaction mechanism of the asymmetric reduction conducted in the presence of a catalyst composed of a complex of the chiral bisphosphine and a transition metal. According to studies on the coordination structure of a bisphosphine-rhodium complex, for example, the structure of an important intermediate of (2S,4S)-N-tertbutoxycarbonyl-4-diphenylphosphino-2-diphenylphosphinomethylpyrrolidine-rhodium (simply named as BPPM) using itaconic acid as substrate in an asymmetric reducing reaction can be shown below:

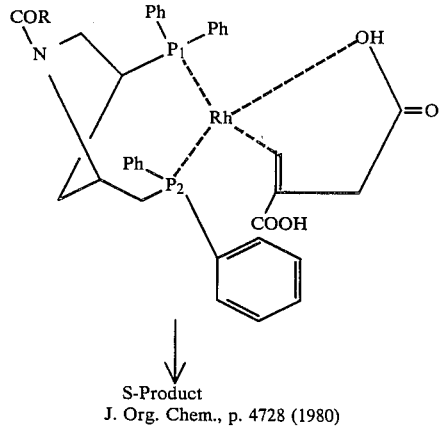

S-Product
J. Org. Chem., p. 4728 (1980)

This complex has such a structure that the diphenylphosphine group ($P_2$) in the cis-position to an olefin to be asymmetrically reduced serves to form a new asymmetric position for asymmetry initiation, while the other diphenylphosphine group ($P_1$) exists in the trans-position to the olefin. In a more specific example for a process for the asymmetric synthesis of R-(—)-pantolactone from ketopantolactone by asymmetric reduction, an important intermediate of the following formula:

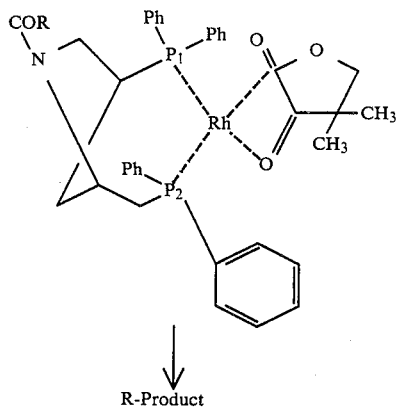

R-Product is considered in this synthetic process [Tetrahedron Letters 4431 (1977);Chemistry Letters 297 (1978)].

The present inventor already synthesized the above-mentioned BPPM as a chiral bisphosphine and used it as a combination with rhodium 1,5-cyclooctadiene chloride complex for asymmetric reduction of ketopantolactone whereby R-(—)-pantolactone was obtained in an optical yield of 80.5% at a reaction efficiency of substrate/Rh=$10^2$ (molar ratio). The optical yield of the product in this case is relatively good but the reaction efficiency was found to be unsatisfactory in industrial point of view. On the other hand, Tani et al. [J. Chem. Soc. Chem. Commun. 1641 (1984)] reported that they synthesized one of the chiral bisphosphines having two dicyclohexylphosphine groups, (2S,4S)-N-acyl-4-dicyclohexylphosphino-2-dicyclohexylphosphinomethylpyrrolidine (BCCP), and used it in the same manner as in the case of BPPM for asymmetric reduction of ketopantolactone whereby R-(—)-pantolactone was obtained in an optical yield of 66% at a reaction efficiency of substrate/Rh=2×10² (molar ratio), t ½=20 min. In contrast to the case of BPPM, the reaction efficiency in this case is somewhat improved but the optical yield is extremely inferior, thus making this process industrially unattractive.

In accordance with the above-described consideration on the coordination structure of the bisphosphine-rhodium complex, the present inventor has synthesized a variety of phosphihopyrrolidine compounds of the general formula (I) or (I'), and used as a combination with rhodium 1,5-cyclooctadiene chloride complex for asymmetrical hydrogenation of ketopantolactone, surmising that the phosphine group (P₂) located in the cis-position to a functional group subjected to asymmetric reaction and believed to give influence on the optical yield of the product while the phosphine group (P₁) located in the transposition to the functional group and believed to give influence on the reaction efficiency (reaction rate). In case of preparing R-(−)-pantolactone, for example, the asymmetric reduction proceeds in an optical yield of 91–95% at a reaction efficiency of substrate/Rh=10⁵ (molar ratio), thus revealing that the reduction reaction is excellent in both optical yield and reaction efficiency to be carried out in an industrial scale.

In order to find technically advantageous combinations of the substituents in the phosphine moieties, several kinds of 2,4-diphosphinopyrrolidine compounds were synthesized and used together with the same rhodium complex compound for the pantolactone as substrate. In one of the tests, the substituents in the phosphine groups in 2- and 4-position of the compound were selected from phenyl group as a typical aryl group and cyclohexyl group as a typical cycloaliphatic hydrocarbyl group. Accordingly, 4 kinds in all of the phosphinopyrrolidine compounds were synthesized in which R² and R³ each represents a phenyl or cyclohexyl group and R⁴ and R⁵ each represents a phenyl or cyclohexyl group, and then used in each case together with rhodium 1,5-cyclooctadiene chloride for asymmetric hydrogenation of ketopantolactone. A result of the test was as shown in Table 1 below wherein Ph, Cy and t-Bu used in the structural formulas mean phenyl, cyclohexyl and tert-butyl, respectively.

TABLE 1

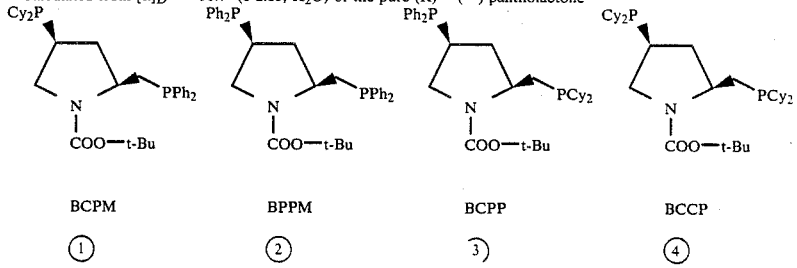

| Ligand | [Substrate]/[Rh] | Conversion rate (%)*ᵃ | $[\alpha]_D^{20-24}$(c 2.0, H₂O) | Optical yield (%)*ᵇ |
|---|---|---|---|---|
| BPPM | 10² | 100 | −40.8° | 81 |
|  | 10³ | 44 | −16.1° | 72 |
| BCPM | 10³ | 100 | −45.9° | 91 |
|  | 10⁴ | 100.0 | −45.6° | 90 |
| BCPP | 10³ | 75 | −3.9° | 9 |
| BCCP | 10⁴ | 100.0 | +30.8° | 61 |

*ᵃAccording to gas chromatography
*ᵇCalculated from $[\alpha]_D^{25}$ −50.7° (c 2.05, H₂O) of the pure (R)-(−)-pantholactone

| BCPM | BPPM | BCPP | BCCP |
|---|---|---|---|
| ① | ② | ③ | ④ |

As is evident from the data shown in Table 1, the 2-diphenylphosphinomethyl-4-dicyclohexylphosphino compound (Ligand BCPM) exhibited the most excellent results in comparison with other similar compounds (Ligands BPPM, BCPP and BCCP).

In the compounds of the general formula (I) or (I') of this invention, the radical R¹ at the ring nitrogen atom in the pyrrolidine ring stands for a hydrogen atom, —COR, —COOR, —CONHR or —SO₂—R wherein R is an alkyl or aryl group. The alkyl group may be linear or branched and preferably has 1-8 carbon atoms. Illustrative of the alkyl group are, for example, methyl, ethyl, propyl, isopropyl, n-butyl, sec-butyl, tert-butyl, n-pentyl, n-hexyl, 2-ethylbutyl, n-heptyl, n-octyl and 2-ethylhexyl. A typical aryl group is phenyl. These alkyl and aryl groups may have one or more halogen atoms, hydroxyl groups and alkoxy groups as substituents. The phenyl group may further have one or more alkyl groups as substituents. Accordingly, preferable examples of R¹ in case of —COR include formyl, acetyl, chloroacetyl, trifluoroacetyl, propionyl, n-butyryl, pivaloyl, pentanoyl, hexanoyl, octanoyl, benzoyl, p-methylbenzoyl, salicyl and p-methoxybenzoyl. Preferable examples of R¹ in case of —COOR include methoxycarbonyl, ethoxycarbonyl, tert-butoxycarbonyl, hexyloxycarbonyl, phenoxycarbonyl and p-methylphenoxycarbonyl. Preferable examples of R¹ in case of —CONHR include N-methylcarbamoyl, N-tert-butylcarbamoyl, N-hexylcarbamoyl, N-phenylcarbamoyl and N-p-methylphenylcarbamoyl. Preferable examples of R¹ in case of —SO₂R include methanesulfonyl, ethanesulfonyl and phenylsulfonyl.

The radicals R² and R³ in the general formula (I) or (I') may be the same or different and are selected from aryl groups which include carbocyclic and heterocyclic aromatic groups. Examples of the carbocyclic aromatic group include phenyl and naphthyl, while those of the heterocyclic aromatic group include furyl, thienyl pyrrolyl, pyridyl, pyrazinyl, pyrimidyl, pyridazinyl, quinolyl and isoquinolyl. These aromatic groups may be substituted on their rings with one or more halogen atoms, hydroxyl group, alkyl groups and alkoxy groups. In a preferable embodiment of the present invention, $R^2$ and $R^3$ are identical and both represent a phenyl group.

The radicals $R^4$ and $R^5$ in the general formula (I) and (I′) may be the same or different and are selected from aliphatic and cycloaliphatic hydrocarbyl groups. Examples of the aliphatic hydrocarbyl group include straight chain or branched chain alkyl, alkenyl and alkynyl groups having 1–8 carbon atoms. Illustrative of the alkyl group are, for example, methyl, ethyl, propyl, n-butyl, sec-butyl, tert-butyl, pentyl, hexyl, heptyl, octyl and 2-ethylhexyl. Illustrative of the alkenyl and alkynyl groups are, for example, allyl, butenyl, pentenyl, hexenyl, octenyl, ethynyl, propynyl and butynyl. Examples of the cycloaliphatic hydrocarbyl group include cycloalkyl, cycloalkenyl and cycloalkynyl groups having 5–8 carbon atoms. Illustrative of the cycloalkyl group are, for example, cyclopentyl, cyclohexyl, cycloheptyl and cyclooctyl. Illustrative of the cycloalkenyl and cycloalkynyl groups are cyclopentenyl, cyclohexenyl, cyclooctenyl, cyclopentynyl and cyclohexynyl. These aliphatic and cycloaliphatic hydrocarbyl groups may have one or more halogen atoms, hydroxyl groups and alkoxy groups. The cycloaliphatic hydrocarbyl groups may also be substituted by one or more alkyl groups. $R^4$ and $R^5$ are preferably identical and are preferably selected from the alkyl groups and cycloalkyl groups. Most preferable as $R^4$ or $R^5$ is a $C_1$–$C_4$ alkyl and a $C_5$–$C_6$ cycloalkyl, especially cyclohexyl.

Preferable examples of the new chiral phosphinopyrrolidine compounds of this invention represented by the general formula (I) or (I′) include:

(2S,4S)- or (2R, 4R)-4-dicyclohexylphosphino-2-diphenylphosphinomethylpyrrolidine (2S,4S)- or (2R,4R)-N-acetyl-4-dicyclohexylphosphino-2-diphenylphosphinomethylpyrrolidine (2S,4S)- or (2R,4R)-N-pivaloyl-4-dicyclohexylphosphino-2-diphenylphosphinomethylpyrrolidine (2S,4S)- or (2R,4R)-N-benzoyl-4-dicyclohexylphosphino-2-diphenylphosphinomethylpyrrolidine (2S,4S)- or (2R,4R)-N-methoxycarbonyl-4-dicyclohexylphosphino-2-diphenylphosphinomethylpyrrolidine (2S,4S)- or (2R,4R)-N-tert-butoxycarbonyl-4-dicyclohexylphosphino-2- diphenylphosphinomethylpyrrolidine (2S,4S)- or (2R,4R)-N-phenoxycarbonyl-4-dicyclohexylphosphino-2-diphenylphosphinomethylpyrrolidine (2S,4S)- or (2R,4R)-N-methylcarbamoyl-4- dicyclohexylphosphino-2-diphenylphosphinomethylpyrrolidine (2S,4S)-or (2R,4R)-N-tert-butylcarbamoyl-4-dicyclohexylphosphino-2-diphenylphosphinomethylpyrrolidine (2S,4S)- or (2R,4R)-N-phenylcarbamoyl-4-dicyclohexylphosphino- 2-diphenylphosphinomethylpyrrolidine (2S,4S)- or (2R,4R)-N-methanesulfonyl-4-dicyclohexylphosphino-2-diphenylphosphinomethylpyrrolidine The new chiral phosphinopyrrolidine compounds of the general formula (I) are prepared according to a series of the steps shown in Scheme 1 wherein the 4-dicyclohexylphosphinoexample-2-diphenylphosphinomethypyrrolidone, compound is given as an example of the compounds of this invention and wherein Ms stands for —SO$_2$—CH$_3$, Cy for cyclohexyl and Ph for phenyl.

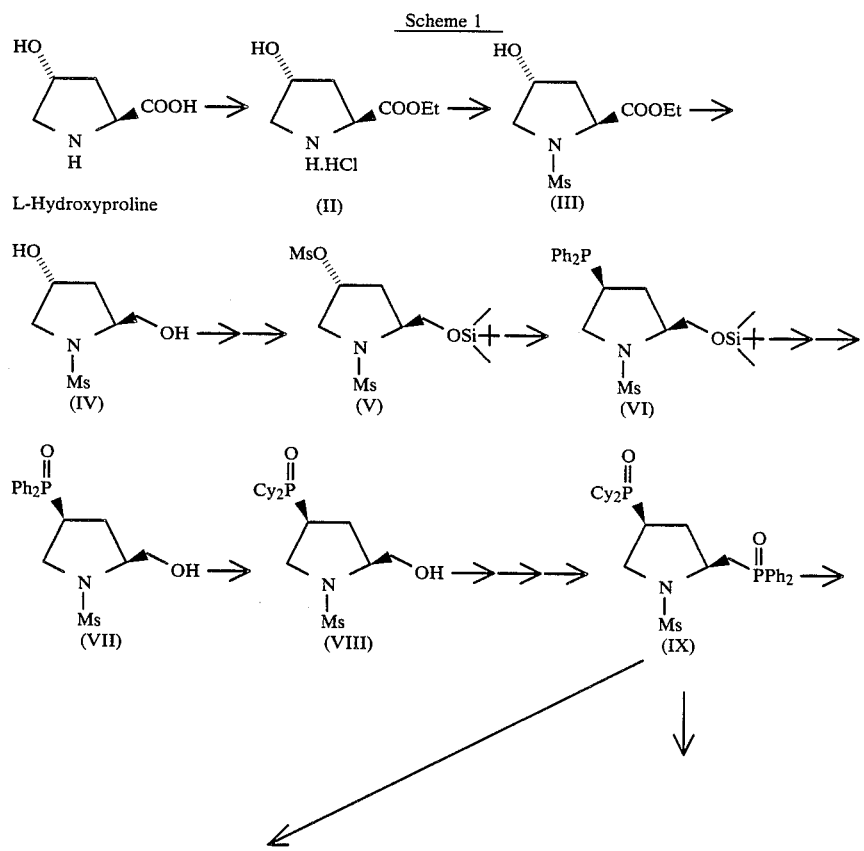

Scheme 1

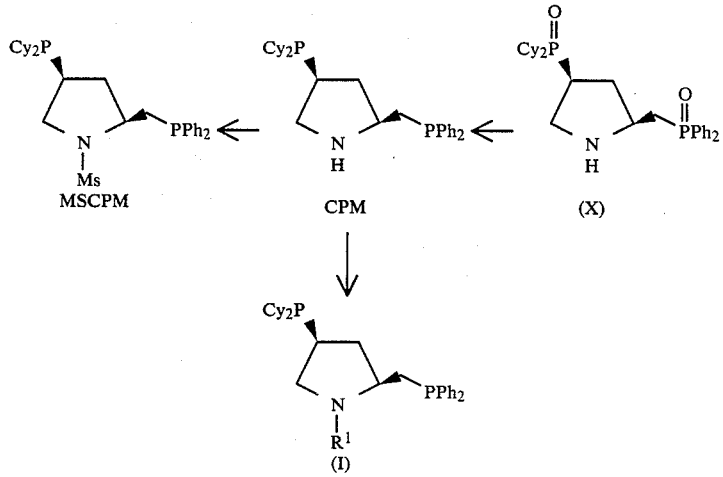

In Scheme 1, the end product, i.e. the compound of the formula (I), has the substituent R¹ at the ring nitrogen atom. The relation between the substituent R¹ and the ligand abbreviations is as follows:

| | | | |
|---|---|---|---|
| R¹ = H | (CPM) | R¹ = CONHCH₃ | (MCCPM) |
| R¹ = SO₂CH₃ | (MSCPM) | R¹ = CONHt-Bu | (BCCPM) |
| R¹ = CO₂t-Bu | (BCPM) | R¹ = CONHPh | (PCCPM) |
| R¹ = CO₂CH₃ | (MCPM) | R¹ = COCH₃ | (ACPM) |
| R¹ = CO₂Ph | (PCPM) | R¹ = COt-Bu | (PVCPM) |
| | | R¹ = COPh | (BZCPM) |

According to the process shown in Scheme 1, L-4-hydroxyproline is first esterified with ethanol or a reactive functional derivative thereof in a usual manner to form L-hydroxyproline ethyl ester hydrochloride (II). This ester (II) is reacted with methanesulfonyl chloride to obtain its N-mesylated derivative (III). This mesylate (III) is then reduced with lithium aluminum hydride to prepare the corresponding 2-hydroxymethyl compound (IV), which is then reacted with tert-butyldimethylsilyl chloride and successively with methanesulfonyl chloride to form the corresponding N-mesyl-2 -tert-butyldimethylsilyloxymethyl-4-mesyloxy compound (V). The compound (V) is reacted with chlorodiphenylphosphine to form the corresponding 4-diphenylphosphino compound (VI). The phosphorus atom in the compound (VI) is oxidized with hydrogen peroxide whereby the silyl group in the 2-position is split off simultaneously to form the oxide (VII). This oxide is then subjected to hydrogenation by the aid of a rhodium catalyst whereby the phenyl rings are hydrogenated to form the corresponding 4-dicyclohexylphosphono compound (VIII). This compound is then reacted with methanesulfonyl chloride to introduce mesyl group into the 2-position and successively reacted with chlorodiphenylphosphine to form the compound (IX). This compound is then reacted with trichlorosilane in the presence of triethylamine to form N-methanesulfonyl-4-dicyclohexylphosphino-2-diphenylphosphinomethylpyrrolidine (MSCPM). This compound can be converted into the corresponding N-unsubstituted compound (CPM) by hydrolysis with a mineral acid such as 48% hydrobromic acid. Alternatively, the compound (IX) is first hydrolyzed with such mineral acid to form the corresponding N-unsubstituted compound (X) which is then reduced with trichlorosilane in the presence of a tertiary amine such as triethylamine to form CPM. Starting from this CPM, various compounds of the general formula (I) can be prepared by reaction with a reagent capable of introducing the desired R¹ into the N-position. For example, CPM is reacted with phenylchlorocarbonate to form PCPM, with phenyl isocyanate to form the compound (I) wherein R¹ is —CONHPh (PCCPM), with acetyl chloride to form the compound (I) wherein R¹ is acetyl (ACPM) or with ditert-butyl carbonate to form the compound (I) wherein R¹ is —COOtert—Bu (BCPM). These reactions per se are known and can be carried out in a usual manner.

The new chiral phosphinopyrrolidine compounds of the general formula (I') are prepared according to a series of the steps shown in Scheme 2 wherein 4-dicyclohexylphosphino-2-diphenylphosphinomethylpyrrolidine compound is given as an example of the compounds of this invention and wherein Ms, Cy and Ph have the same meanings as given in Scheme 1, Ac stands for CH₃CO—, Et for ethyl, Py for pyridine, and Me for methyl.

Scheme 2

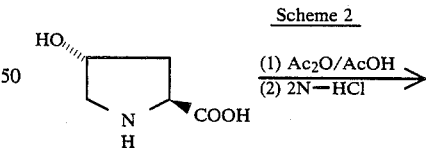

L-Hydroxyproline

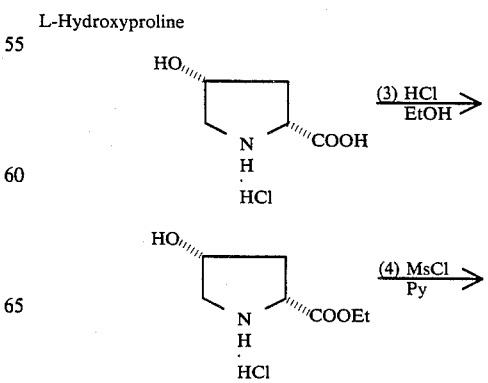

-continued
Scheme 2

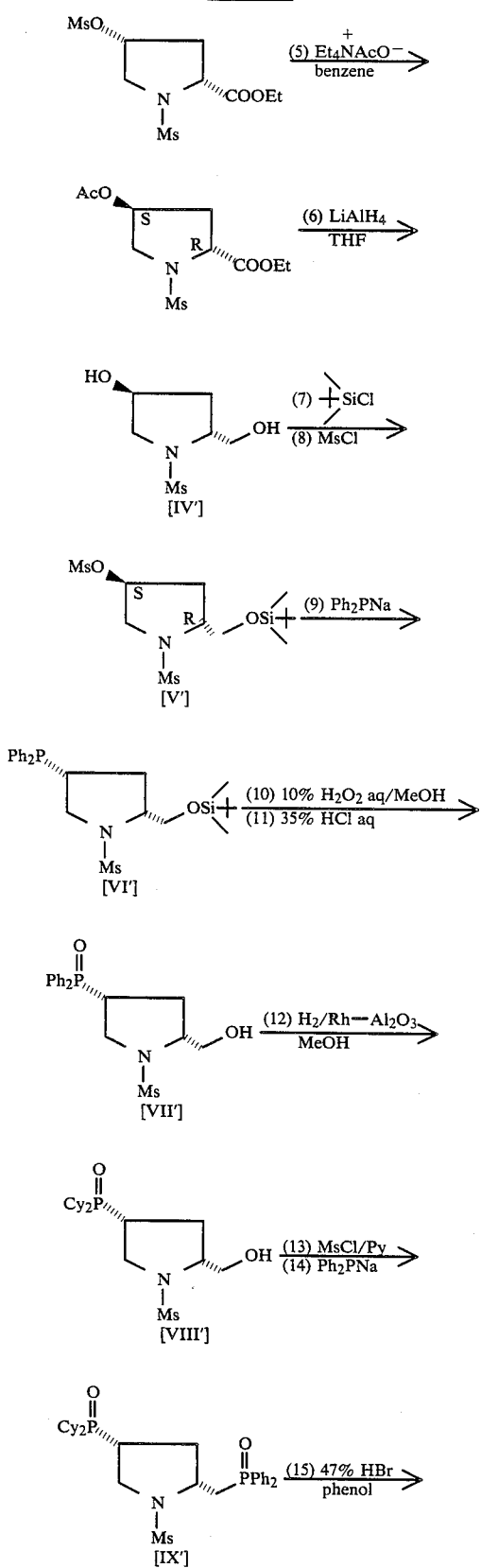

-continued
Scheme 2

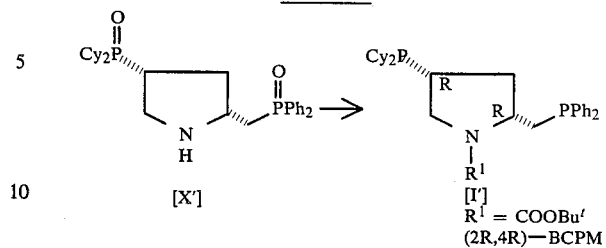

According to the process shown in Scheme 2, allo-4-hydroxy-D-proline ethyl ester hydrochloride is first synthesized from L-4-hydroxyproline in accordance with the method disclosed in J. Org. Chem. 46 (1981), 2954 involving the steps of reacting L-4-hydroxyproline with $Ac_2O$/AcOH and then with 2N-HCl to form allo-4-hydroxy-D-proline hydrochloride and reacting it with ethanol saturated with hydrogen chloride.

This starting compound is reacted with methanesulfonyl chloride to form (2R,4R)-N-methanesulfonyl-4-methanesulfonyloxyproline ethyl ester, which is then reacted with tetraethylammonium acetate to form (2R,4S)-N-methanesulfonyl-4-acetoxyproline ethyl ester. This compound is reduced with lithium aluminum hydride to obtain (2R,4S)-N-methanesulfonyl-4-hydroxy-2-hydroxymethylpyrrolidine (IV'). This compound (IV') can then be converted into the end compound (I') in the same manner as in the case of converting the (2S,4R)-N-mesyl-4-hydroxy-2-hydroxymethylpyrrolidine (IV) into the compound (I) through the compounds (V), (VI), (VII), (VIII), (IX) and (X) in the foregoing Scheme 1.

The new chiral phosphinopyrrolidine compounds of this invention are extremely valuable as ligands for catalytic asymmetric hydrogenation of reducible compounds having in their molecule structure —C═C—, —C═N— and/or >C═O double bond in the asymmetric synthesis of optically active compounds. The reducible compounds in this case must have the above mentioned double bond to be hydrogenated but are so chosen that the reduced compounds may have an asymmetric carbon atom in their reduced site. Examples of the reducible compounds include those having a carbon-to-oxygen double bond, for example, α-ketoacids such as ketopantolactone and pyruvic acid esters, β-ketoacids such as ethyl acetoacetate, α-aminoketones such as phenacylamine hydrochloride, α-hydroxyketones such as phenacyl alcohol; those having a carbon-to-carbon double bond such as itaconic acid; and those having a carbon-to-nitrogen double bond such as acetobenzylimine. A process for the asymmetric synthesis of optically active compounds by catalytic reduction of the reducible compounds with the aid of the compound of this invention as a ligand together with the reaction metal catalyst will now be explained hereinafter, taking up the asymmetric synthesis of pantolactone from ketopantolactone as an example.

A solvent generally employed for catalytic reduction can also be used for the asymmetric synthesis. For example, water, a water-miscible alcohol such as methanol, ethanol or isopropanol, acetic acid or propionic acid, an ester such as ethyl acetate, an ether such as tetrahydrofuran or dioxane, or an aromatic hydrocarbon such as benzene or toluene can be used advantageously. In 50 ml of such solvent are dissolved 100 m-mol of ketopantolactone and 0.01–0.001 m-mol of the phosphinopyrrolidine compound of this invention as a ligand. A rhodium metal complex compound such as rhodium 1,5-hexadiene chloride complex or rhodium 1,5-octadiene chloride complex in an amount of 0.005–0.0005 m-mol is added to the solution and the mixture is subjected to hydrogenation reaction at atmospheric or super-atmospheric pressure at a reaction temperature of about 20° C. After completion of the reaction, the solvent used is distilled off and the residual substance is worked up properly whereupon D-pantolactone can be obtained as the product in a high yield. In such typical hydrogenation reaction, the metal complex compound and the ligand can be added separately to the reaction system or may be added, if desired, in the form of a composition previously prepared from the metal complex compound and the ligand. If necessary, an auxiliary substance such as triethylamine may be added to the reaction system to accelerate the hydrogenation reaction. The method and operation per se for the above catalytic hydrogenation are conducted in a conventional manner employed for ordinary catalytic reduction. No particular process is unnecessary for carrying out the asymmetric reduction of the reducible compounds.

The phosphinopyrrolidine compounds of this invention are utilizable as ligands together with a metal complex compound as catalyst for the asymmetric synthesis of optically active compounds from the reducible compounds by asymmetric catalytic reduction, whereby high levels of optical yield and reaction efficiency which are quite unexpected from the prior art asymmetric reduction techniques can be attained. Thus, the compounds of this invention can advantageously be used for the asymmetric synthesis of industrially important optically active substances. For example, the compounds of this invention can be used for the asymmetric synthesis of D-pantolactone from ketopantolactone in an extremely high optical yield at an industrially attractive high reaction efficiency.

The present invention will now be illustrated in more detail by way of examples. Examples 1–12 illustrate the preparation of the new chiral phosphinopyrrolidine compounds of this invention.

EXAMPLE 1

Preparation of MSCPM (a) Preparation of (2S,4R)-N-methanesulfonyl-4-hydroxyproline ethyl ester [III]

In 200 ml of pyridine was placed 19.56 g (0.1 mol) of (2S,4R)-4-hydroxyproline ethyl ester hydrochloride, and 12.03 g (0.105 mol) of methanesulfonyl chloride was slowly added dropwise to the mixture under agitation and ice-cooling. After stirring the mixture under ice-cooling for 6 hours, the mixture was further stirred overnight at room temperature. After distilling off the pyridine under reduced pressure, 10% hydrochloric acid was added to the reaction mixture under ice-cooling. The mixture was extracted three times with 200 ml of ethyl acetate in each case and the ethyl acetate extracts were combined, washed with 40 ml of a saturated aqueous solution of sodium chloride and then dried over magnesium sulfate. The extract was concentrated under reduced pressure and dried until dryness whereby a solid substance having a melting point of 111°–113° C. was obtained in a yield of 18.7 g (78.9%) which, after recrystallization from ethyl acetate, showed a melting point of 118°–120° C.

(b) Preparation of (2S,4R)-N-methanesulfonyl-4-hydroxy-2-hydroxymethylpyrrolidine [IV]

To 360 ml of tetrahydrofuran was added 3.98 g (0.105 mol) of lithium aluminum hydride, and the mixture was stirred. To this mixture was slowly added dropwise a solution of 16.6 g (0.07 mol) of (2S,4R)-N-methanesulfonyl-4-hydroxyproline ethyl ester [III] in 200 ml of tetrahydrofuran under agitation and ice-cooling. After stirring the suspension at 0° C. for 3 hours and then at room temperature for 3 hours, 14 ml of water was added dropwise in small portions to the suspension under ice-cooling, and thereafter the mixture was stirred for 30 minutes. Any insoluble matter was removed by filtration and the filtrate was concentrated until dryness under reduced pressure whereby 11.9 g (yield: 87%) of an oily substance was obtained.

(c) Preparation of (2S,4R)-N-methanesulfonyl-2-tert-butyldimethylsilyloxymethyl-4-methanesulfonyloxypyrrolidine [V]

To 160 ml of tetrahydrofuran were added 7.81 g (0.04 mol) of (2S,4R)-N-methanesulfonyl-4-hydroxy-2-hydroxymethylpyrrolidine [IV] 195 mg (1.6 m-mol) of 4-dimethylaminopyridine and 4.86 g (0.048 mol) of triethylamine, and the mixture was stirred. To this mixture was added 6.63 g (0.044 mol) of tert-butylmethylsilyl chloride, and the whole was stirred overnight at room temperature. After concentrating the reaction mixture under reduced pressure, 40 ml of water was added to the residue and the organic phase was taken up with 120 ml of ethyl acetate three times. The extract was washed with 40 ml of a saturated solution of sodium chloride and dried over magnesium sulfate and concentrated until dryness under reduced pressure. The residue was dissolved in 100 ml of pyridine and 5.05 g (0.044 mol) of methanesulfonyl chloride was slowly added dropwise to the mixture under agitation and icecooling. The mixture was allowed to stand overnight and then incorporated under ice-cooling with 400 ml of 10% hydrochloric acid. The mixture was extracted with 150 ml of ethyl acetate three times and the extract was washed with 75 ml of a saturated aqueous solution of sodium hydrogen carbonate and then with 75 ml of a saturated aqueous solution of sodium chloride and dried over magnesium sulfate. The extract was concentrated until dryness under reduced pressure to obtain 12.56 g (yield: 81%) of an oily substance which, after recrystallization from a mixture of isopropyl ether and n-hexane, gave crystals having a melting point of 51.5°–52.5° C. $[\alpha]_D^{20} = -28.57°$ (c=1, EtOH)

(d) Preparation of (2S,4S)-N-methanesulfonyl-2-tert-butyldimethylsilyloxymethyl-4-diphenylphosphinopyrrolidine [VI]

To 150 ml of dioxane were added 11.39 g (0.052 mol) of chlorodiphenylphosphine and 2.6 g (0.114 mol) of sodium, and the mixture was refluxed for 4 hours in nitrogen atmosphere. After allowing the mixture to stand for cooling, 50 ml of tetrahydrofuran was added to the reaction mixture, and a solution of 10.45 g (0.027 mol) of (2S,4R)-N-methanesulfonyl-2-tert-butyldimethylsilyloxymethyl-4-methanesulfonyloxypyrrolidine [V] in 100 ml of tetrahydrofuran was added dropwise to the mixture lest any air should enter in the reaction system. The mixture was stirred in nitrogen atmosphere at 0° C. for 2 hours and then at room temperature overnight and then any insoluble matter was removed, for example, by filtration. The filtrate was concentrated until dryness under reduced pressure and the residue was purified by column chromatography on silica gel whereby 7.93 g (yield: 62%) of an oily substance was obtained.

(e) Preparation of (2S,4S)-N-methanesulfonyl-4-diphenylphosphinyl-2-hydroxymethylpyrrolidine [VII]

In 180 ml of methanol was dissolved 8.39 g (0.0176 mol) of 2S,4S)-N-methanesulfonyl-2 -tert-butyldimethlysilyloxymethyl-4-di-phosphinopyrrolidine [VI], and 11.85 g (0.0348 mol) of 10% hydrogen peroxide was added dropwise to the solution under ice-cooling. The mixture was stirred at 0° C. for one hour and then at room temperature for one hour. To the mixture was then slowly added dropwise a liquid mixture of 8.6 g of 35% hydrochloric acid, 52.7 g of water and 38.7 g of methanol, and the mixture was stirred for 2 hours at room temperature. Any insoluble matter was removed from the mixture by filtration and the filtrate was concentrated under reduced pressure. The concentrate was dissolved in 50 ml of water and the aqueous solution was extracted three times with 100 ml of methylene chloride in each case. The extract was washed with a saturated solution of sodium hydrogen carbonate, dried over magnesium sulfate and concentrated under reduced pressure whereby white crystals were obtained which were then recrystallized from a mixture of ethanol and isopropyl alcohol. Yield 5.3 g (80%), melting point: 138°–139° C.

(f) Preparation of (2S,4S)-N-methanesulfonyl-4-dicyclohexylphosphinyl-2-hydroxymethylpyrrolidine [VII]

An autoclave was charged with 1.70 g (4.5 m-xol) of (2S,4S)-N-methanesulfonyl-4-diphenylphosphinyl-2-hydroxymethylpyrrolidine [VII], 850 mg of 5% Ph/Al$_2$O$_3$ and 20 ml of methanol, and the mixture was stirred for 2 days at 150° C. under 150 atm. pressure of hydrogen. The reaction mixture was subjected to microfiltration and the filtrate was concentrated and subjected to column chromatography on silica gel (solvent: ethanol) to be separated from a fraction insoluble in the organic solvent. The eluent was concentrated until dryness under reduced pressure whereby 1050 g (yield: 84%) of crystals were obtained.

(g) Preparation of (2S,4S)-N-methanesulfonyl-4-cyclohexylphosphinyl-2-diphenylphosphinylmethylpyrrolidine [IX]

In 20 ml of pyridine was dissolved 1.4 g (3.6 m-mol) of (2S,4S)-N-methanesulfonyl-4-dicyclohexylphosphinyl-2-hydroxymethylpyrrolidine [VIII], and 0.82 g (7.2 m-xol) of methanesulfonyl. chloride was added dropwise to the solution under ice-cooling. After stirring the mixture at 0° C. for 3 hours and then at room temperature overnight, 70 ml of 10% hydrochloric acid was added to the mixture under ice-cooling. The mixture was extracted three times with 80 ml of ethyl acetate, and the extract was washed with 30 ml of a saturated solution of sodium hydrogen carbonate and with 30 ml of water and dried over magnesium sulfate. The extract was concentrated under reduced pressure to obtain 1.24 g (yield: 74%) of (2S,4S)-N-methanesulfonyl-4-dicyclohexylphosphinyl-2-methanesulfonyloxymethylpyrrolidine as white crystals. Besides this, 1.88 g (8.52 m-mol) of chlorodiphenylphosphine and 392 mg (17.04 m-mol) of metallic sodium were added to 20 ml of dioxane and the mixture was refluxed in nitrogen atmosphere for 3 hours. After allowing the mixture to stand for cooling, 20 ml of tetrahydrofuran was added to the mixture, and a solution of the previously obtained crystals in 20 ml of dimethylformamide was added dropwise to the mixture at −20° C. to −30° C. lest any air should enter in the reaction system. The mixture was stirred overnight at −20° C. to −30° C. in nitrogen atmosphere, separated from insoluble matters and concentrated under reduced pressure. The residue was extracted three times with 50 ml of ethyl acetate and the extract was washed with 50 ml of water and concentrated under reduced pressure. Using 2.45 g (7.2 m-mol) of 10% hydrogen peroxide, the operation was carried out in the same manner as described in Example 1(e) whereby the title compound was obtained as crystals. Yield 982 mg (80%).

(h) Preparation of (2S,4S)-N-methanesulfonyl-4-dicyclohexylphosphino-2-diphenylphosphinomethylpyrrolidine (MSCPM)

In 8 ml of acetonitrile were dissolved 115 mg (0.2 m-mol) of (2S,4S)-N-methanesulfonyl-4-dicyclohexylphosphinyl-2-diphenylphosphinylmethylpyrrolidine [IX] and 85 mg (0.84 m-mol) of triethylamine, and the air in the reaction vessel was completely replaced with nitrogen. To this mixture under ice-cooling was added dropwise a solution of 108 mg (0.8 m-mol) of trichlorosilane in 2 ml of acetonitrile. After refluxing the mixture for 3 hours, the reaction liquid was warmed to room temperature and then concentrated under reduced pressure. The resultant product was dissolved in 15 ml of benzene and 10 ml of a 30% aqueous solution of caustic soda was added to the solution under ice-cooling. The mixture was stirred at 50°–60° C. for 30 minutes in nitrogen atmosphere. The benzene layer was separated and the aqueous layer was extracted with 10 ml of benzene. The benzene extract was combined with the benzene layer and the combined benzene phase was washed with 10 ml of water, dried over magnesium sulfate and concentrated under reduced pressure. A mixture of ethanol and n-hexane was added to the residue for crystallization whereby 87 mg (yield: 80%) of the product was obtained which had a melting point of 139°–142° C. and $[\alpha]_D = -57.9°$ (c=1.0, benzene).

IR: 1343 cm$^{-1}$(SO$_2$), 1150 cm$^{-1}$ (SO$_2$).

NMR (CDCl$_3$),δ. 0.83–1.95 (22H, m, (C$_6$H$_{11}$)$_2$). 1.97–2.48 (3H, m, CCH$_2$C, CH$_a$H$_b$P, H$_a$ or H$_b$). 2.60–2.85 (1H, m, >PCH). 2.76 (3H, s, SO$_2$CH$_3$). 2.90–3.36 (2H, m, H$_a$ or H$_b$, CH$_c$H$_d$N, H$_c$ or H$_d$). 3.44–4.04 (2H, m, H$_c$ or H$_d$, NCH). 7.12–7.64 (10H, m, (C$_6$H$_5$)$_2$).

EXAMPLE 2

Preparation of CPM (a) Preparation of (2S,4S)-4-dicyclohexylphosphinyl-2-diphenylphosphinylmethylpyrrolidine [X]

(2S,4S)-N-methanesulfonyl-4-dicyclohexylphosphinyl-2 -diphenylphosphinylmethylpyrrolidine [IX] in an amount of 350 mg was mixed with and dissolved in 700 mg of phenol and 5.3 ml of 48% hydrobromic acid, and the solution was refluxed in nitrogen atmosphere for 8–10 hours. After completion of the reaction, the solution was made alkaline with a 30% aqueous solution of caustic soda and was then extracted three times with 20 ml of ethyl acetate in each case. The extract was washed with 20 ml of water and then with 20 ml of a saturated solution of sodium chloride, dried over magnesium sulfate and concentrated under reduced pressure. The residue was purified by way of column chromatography on silica gel whereby 196 mg (yield: 65%) of the title compound was obtained as crystals.

(b) Preparation of (2S,4S)-4-dicyclohexylphosphino-2-diphenylphosphinomethylpyrrolidine (CPM)

In 4 ml of acetonitrile were dissolved 50 mg (0.1 m-mol) of (2S,4S)-4-dicyclohexylphosphinyl-2-diphenylphosphinylmethylpyrrolidine [X] and 42 mg (0.42 m-mol) of triethylamine, and the air in the reaction vessel was satisfactorily replaced with nitrogen. A solution of 54 mg (0.4 m-mol) of trichlorosilane in 1 ml of acetonitrile was added dropwise to the above solution under ice-cooling. After refluxing the mixture for 3 hours, the mixture was concentrated under reduced pressure at a low temperature. The residual product was dissolved in 15 ml of benzene, and 10 ml of a 30% aqueous solution of caustic soda was added to the benzene solution under ice-cooling. The mixture was stirred in nitrogen atmosphere for 30 minutes at 50°60° C. The benzene phase was separated and the aqueous phase was extracted with 10 ml of benzene. The benzene phases are combined, washed with 10 ml of water, dried over magnesium sulfate and concentrated under reduced pressure whereby 44 mg (yield: 95%) of the title compound was obtained.

EXAMPLE 3

Preparation of (2S,4S)-N-phenylcarbamoyl-4-dicyclohexylphosphino-2-diphenylphosphinomethyl pyrrolidine (PCCPM)

In 1 ml of methylene chloride was dissolved 46 mg (0.1 m-mol) of CPM obtained in Example 2. To this solution was added dropwise a solution of 13 mg (0.11 m-mol) of phenyl isocyanate in 2 ml of methylene chloride, and the mixture was stirred in nitrogen atmosphere for 2-3 hours at room temperature. The reaction liquid was concentrated under reduced pressure whereby 50 mg (yield: 86%) of the title compound was obtained as white crystals

EXAMPLE 4

Preparation of (2S,4S)-N-tert-butoxycarbonyl-4-dicyclohexylphosphino-2-diphenylphosphinomethyl pyrrolidine (BCPM)

A treatment was carried out in the same manner as described in Example 3 except that 11 mg (0.11 m-mol) of triethylamine and a solution of 24 mg (0.11 m-mol) of di-tert-butyl dicarbonate in 2 ml of methylene chloride were used in place of the phenyl isocyanate, whereby 48 mg (yield: 85%) of the title compound was obtained as white crystals.

EXAMPLE 5

Preparation of (2S,4S)-N-aetyl-4-dicyclohexylphosphino-2-diphenylphosphinomethylpyrrolidine (ACPM)

A treatment was carried out in the same manner as described in Example 3 except that 22 mg (0.22 m-mol) of triethylamine and 11 mg (0.11 m-mol) of acetic anhydride were used in place of the phenyl isocyanate, whereby 45 mg (yield: 88%) of the title compound was obtained as white crystals.

EXAMPLE 6

Preparation of (2S,4S)-N-methoxycarbonyl-4-dicyclohexylphosphino-2-diphenylphosphinomethyl pyrrolidine (MCPM)

A treatment was carried out in the same manner as described in Example 3 except that 24 mg (0.24 m-mol) of triethylamine and 11 mg (0.12 m-mol) of methyl chlorocarbonate were used in place of the phenyl isocyanate, whereby 43 mg (yield: 83%) of the title compound was obtained as white crystals.

EXAMPLE 7

Preparation of (2S,4S)-N-methylcarbamoyl-4-dicyclohexylphosphino-2-diphenylphosphinomethylpyrrolidine (MCCPM)

Using 300 mg (0.60 m-mol) of (2S,4S)-4-dicyclohexylphosphinyl-2-diphenylphosphinylmethylpyrrolidine, the reaction and after-treatment were carried out in the same manner as described in Example 2(b) to obtain CPM. This CPM was dissolved in 8 ml of methylene chloride and 38 mg (0.66 m-mol) of methyl isocyanate was slowly added dropwise to the solution under ice-cooling. The mixture was stirred in a stream of argon for 2 hours at room temperature. The reaction liquid was concentrated at a lower temperature under reduced pressure, and the residue was dried. This product was recrystallized from methanol to obtain 292 mg (yield: 96%) of MCCPM as white crystals.

EXAMPLE 8

Preparation of (2S,4S)-N-phenoxycarbonyl-4-dicyclo-hexylphosphino-2-diphenylphosphinomethylpyrrolidine (PCPM)

CPM obtained in the same manner as described in Example 7 was dissolved in 8 ml of benzene, and 146 mg (1.39 m-mol) of triethylamine was added to the solution. Under ice-cooling, 103 mg (0.66 m-mol) of phenyl chlorocarbonate was slowly added dropwise to the solution, and thereafter the mixture was stirred for 2 hours at room temperature. The reaction mixture was washed with an aqueous solution of sodium bicarbonate, dried over MgSO$_4$ and then concentrated until dryness. The residual product was recrystallized from ethanol whereby 252 mg (yield: 72%) of PCPM was obtained as yellowish white crystals.

EXAMPLE 9

Preparation of (2S,4S)-N-benzoyl-4-dicyclohexylphosphino-2-diphenylphosphinomethylpyrrolidine (BZCPM)

A treatment was carried out in the same manner as described in Example 8 except that benzoyl chloride was used in place of phenyl chlorocarbonate whereby 281 mg (yield: 82%) of BZCPM was obtained as white crystals after recrystallization of the product from ethanol.

EXAMPLE 10

Preparation of (2S,4S)-N-pivaloyl-4-dicyclohexyl-phosphino-2-diphenylphosphinomethylpyrrolidine (PVCPM)

A treatment was carried out in the same manner as described in Example 8 except that 80 mg (0.66 m-mol) of pivaloyl chloride was used in place of phenyl chlorocarbonate whereby 271 mg (yield: 82%) of PVCPM was obtained as white crystals after recrystallization of the product from ethanol.

EXAMPLE 11

Preparation of (2S,4S)-N-tert-butylcarbamoyl-4-dicyclohexylphosphino-2-diphenylphosphinomethylpyrrolidine (BCCPM)

A treatment was carried out in the same manner as described in Example 7 except that tert-butyl isocyanate was used in place of methyl isocyanate whereby 240 mg (yield: 71%) of BCCPM was obtained as white crystals after recrystallization of the product from ethanol.

EXAMPLE 12

Preparation of (2R,4R)-N-tert-butoxycarbonyl-4-dicyclohexylphosphino-2-diphenylphosphinomethylpyrrolidine (R-BCPM)

In 120 ml of pyridine was dissolved 11.74 g (0.06 mol) of allo-4-hydroxy-D-proline ethyl ester hydrochloride prepared according to the method disclosed in J. Org. Chem., 46 (1981), 2954, and the solution was stirred. Under ice-cooling, 17.2 g (0.15 mol) of methanesulfonyl chloride was slowly added dropwise to the solution under agitation. The reaction mixture was allowed to stand overnight. The pyridine was removed from the reaction mixture by distillation under reduced pressure and 10% hydrochloric acid was added to the reaction mixture under ice-cooling. The mixture was then extracted three times with 120 ml of ethyl acetate and the extract was washed with a saturated solution of edible salt, dried over magnesium sulfate and concentrated under reduced pressure whereby 18.26 g of a syrup of (2R,4R)-N-methanesulfonyl-4-methanesulfonyloxyproline ethyl ester was obtained. This compound was added to a solution of 17.3 g (0.066 mol) of tetraethylammonium acetate tetrahydrate in 150 ml of benzene which solution had been refluxed overnight in a water-separator. The mixture was refluxed for one hour and then cooled. The reaction mixture was incorporated with 150 ml of ethyl acetate and 60 ml of water and subjected to phase separation. The ethyl acetate fraction was washed with a saturated solution of edible salt, dried over magnesium sulfate and concentrated under reduced pressure to obtain a syrup, which was then purified by way of column chromatography on 300 g of silica gel, using ethyl acetate-benzene (1:4–1:2) as eluent whereby 11.97 g of a syrup of (2R,4S)-N-methanesulfonyl-4-acetoxyproline ethyl ester was obtained. This compound was dissolved in 100 ml of tetrahydrofuran and the solution was added dropwise to a suspension which had been prepared by adding 4.07 g (0.107 mol) of lithium aluminum hydride in nitrogen atmosphere at 0° C. to 500 ml of tetrahydrofuran. The mixture was stirred for 3 hours under ice-cooling and then for 3 hours at room temperature. The reaction mixture was again ice-cooled and 20 ml of water was added dropwise thereto. The mixture was stirred for 30 minutes at room temperature and any insoluble matter was removed therefrom. The reaction mixture was concentrated under reduced pressure whereby 8.43 g of (2R,4S)-N-methanesulfonyl-4-hydroxy-2-hydroxymethylpyrrolidine [IV'] was obtained as a syrup. Using this compound, a treatment was carried out in the same manner as described in Example 1(c) whereby (2R,4S)-N-methanesulfonyl-2-tert-butyldimethylsilyloxymethyl-4-methanesulfonyloxypyrrolidine [V'] was obtained as crystals having a melting point of 55°–56.5° C. $[\alpha]_D^{23} = +25.8°$ (c=1, EtOH).

Using 11.63 g (0.03 mol) of the compound [V'], a treatment was carried out in the same manner as described in Example 1(d), 1(e), 1(f) and 1(g) whereby 7.51 g (0.013 mol) of (2R,4R)-N-methanesulfonyl-4-dicyclohexylphosphinyl-2-diphenylphosphinylmethylpyrrolidine [IX'] was obtained as crystals.

Using 200 mg of this compound [IX'], a treatment was carried out in the same manner as described in Examples 2 and 4 whereby (2R,4R)-N-tert-butoxycarbonyl-4-dicyclohexylphosphino-2-diphenyl-phosphinomethylpyrrolidine (R-BCPM) was obtained as crystals. m.p. 174°–177° C., $[\alpha]_D^{20} = +38.9°$ (c=1, benzene).

Table 2 shows the characteristic physical properties of the new compounds of this invention illustrated in Examples 3–12.

The following Examples 13–31 illustrate the use of the compounds of this invention as ligands for asymmetric synthesis of various optically active compounds.

EXAMPLE 13

Catalytic asymmetric reduction of ketopantolactone

To 50 ml of tetrahydrofuran were added 12.8 g (100 m-mol) of ketopantolactone, 1 mg (0.0025 m-mol) of rhodium 1,5-cyclooctadiene chloride complex compound and 3.1 mg (0.0055 m-mol) of (2S,4S)-N-tert-butoxycarbonyl-4-dicyclohexylphosphino-2-diphenylphosphinomethylpyrrolidine (BCPM) obtained in Example 4. An autoclave equipped with a stirrer, a pressure gauge and a thermometer was charged with the above mixture and stirred and vibrated at room temperature in hydrogen atmosphere at an initial pressure of 50 atm.

TABLE 2

| Formula of the compound | m.p. (°C.) | $[\alpha]_D$ | IR $\nu_{max}^{KBr}$ cm$^{-1}$ | $^1$H-NMR($\delta$, CDCl$_3$) |
|---|---|---|---|---|
| (BCPM) Cy$_2$P-pyrrolidine-PPh$_2$, N-COO-t-Bu | 171~174 | −41.0° (20° C.) (c 1.00, benzene) | 1685 (CO) | 0.97~1.95(22H, m, P(C$_6$H$_{11}$)$_2$, 1.43(9H, s, (CH$_3$)$_3$), 1.98~2.50(3H, m, CCH$_2$C, H$_a$ or H$_b$ of CH$_2$P), 2.72~3.22 (2H, m, H$_a$ or H$_b$ of CH$_2$P, PCH), 3.52~4.07(3H, m, CH$_2$NCH), 7.15~7.70(10H, m, P(C$_6$H$_5$)$_2$) |
| (R—BCPM) Cy$_2$P-pyrrolidine-PPh$_2$, N-COO-t-Bu | 174~177° C. | +38.9°(20° C.) (c 1.00, benzene) | 1685 (CO) | 0.97~1.95(22H, m, P(C$_6$H$_{11}$)$_2$, 1.43(9H, s, (CH$_3$)$_3$), 1.98~2.50(3H, m, CCH$_2$C, H$_a$ or H$_b$ of CH$_2$P), 2.72~3.22 (2H, m, H$_a$ or H$_b$ of CH$_2$P, PCH), 3.52~4.07(3H, m, CH$_2$NCH), 7.15~7.70(10H, m, P(C$_6$H$_5$)$_2$) |
| (MCCPM) Cy$_2$P-pyrrolidine-PPh$_2$, N-CONHCH$_3$ | 142~143.5 | −29.7°(23° C.) (c 0.60, benzene) | 3320 (NH) 1625 (CO) | 0.75~2.47(25H, m, P(C$_6$H$_{11}$)$_2$, CCH$_2$C, H$_a$ or H$_b$ of CH$_2$P), 2.72(3H, d, J=4.2Hz, CH$_3$), 2.77 (1H, s, NH), 2.90~3.31(2H, m, H$_a$ or H$_b$ of CH$_2$P, PCH), 3.46~4.09(3H, m, CH$_2$NCH), 7.22~7.86(10H, m, P(C$_6$H$_5$)$_2$) |
| (PCCPM) Cy$_2$P-pyrrolidine-PPh$_2$, N-CONHPh | 183~184 | −30.8°(21° C.) (c 1.00, benzene) | 3280 (NH) 1643 (CO) | 0.89~1.98(22H, m, P(C$_6$H$_{11}$)$_2$), 2.00~2.55 (3H, m, CCH$_2$C, H$_a$ or H$_b$ of CH$_2$P), 2.82~3.01(1H, m, PCH), 3.06~4.29(4H, m, H$_a$ or H$_b$ of CH$_2$P, CH$_2$NCH) 5.79~6.00(1H, m, NH), 6.90~7.68(15H, P(C$_6$H$_5$)$_2$, N(C$_6$H$_5$)) |
| (BCCPM) Cy$_2$P-pyrrolidine-PPh$_2$, N-CONH-t-Bu | 160~161 | −15.6°(20° C.) (c 1.00, benzene) | 3450 (NH) 1643 (CO) | 0.93~2.48(25H, m, P(C$_6$H$_{11}$)$_2$, CCH$_2$C, H$_a$ or H$_b$ of CH$_2$P), 1.28(9H, s, (CH$_3$)$_3$), 2.69~3.41(2H, H$_a$ or H$_b$ of CH$_2$P, PCH), 3.48(1H, brs, NH), 3.59~4.67(3H, m, CH$_2$NCH), 7.22~7.62(10H, m, P(C$_6$H$_5$)$_2$) |
| (MCPM) Cy$_2$P-pyrrolidine-PPh$_2$, N-COOCH$_3$ | 149~151 | −52.8°(21° C.) (c 0.50, benzene) | 1694 (CO) | 0.84~2.53(25H, m, P(C$_6$H$_{11}$)$_2$, CCH$_2$C, H$_a$ or H$_b$ of CH$_2$P), 2.72~3.36(2H, m, H$_a$ or H$_b$ of CH$_2$P, PCH), 3.64(3H, s, CH$_3$), 3.45~4.14(3H, m, CH$_2$NCH), 7.12~7.71(10H, m, P(C$_6$H$_5$)$_2$) |
| (PCPM) Cy$_2$P-pyrrolidine-PPh$_2$, N-COOPh | ca. 120 (decomp.) | −44.5°(22° C.) (c 0.82, benzene) | 1719 (CO) | 0.81~2.58(25H, m, P(C$_6$H$_{11}$)$_2$, CCH$_2$C, H$_a$ or H$_b$ of CH$_2$P), 2.80~3.51(2H, m, H$_a$ or H$_b$ of CH$_2$P, PCH), 3.54~4.26(3H, m, CH$_2$NCH), 6.76~7.72(15H, m,p(C$_6$H$_5$)$_2$ O(C$_6$H$_5$)) |

TABLE 2-continued

| Formula of the compound | m.p. (°C.) | $[\alpha]_D$ | IR$\nu_{max}^{KBr}$cm$^{-1}$ | $^1$H-NMR($\delta$, CDCl$_3$) |
| --- | --- | --- | --- | --- |
| 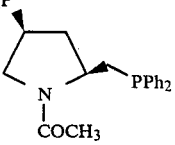 (ACPM) | 169~172 | −16.3°(23° C.) (c 0.40, benzene) | 1642 (CO) | 0.80~2.66(25H, m, P(C$_6$H$_{11}$)$_2$, CCH$_2$C, H$_a$ or H$_b$ of CH$_2$P), 1.95(3H, s, CH$_3$), 3.00~3.43(2H, m, H$_a$ or H$_b$ of CH$_2$P, PCH), 3.47~4.35(3H, m, CH$_2$NCH), 7.17~7.77 (10H, m, P(C$_6$H$_5$)$_2$) |
| 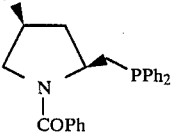 (BZCPM) | 223~224 | −74.5°(23° C.) (c 0.50, benzene) | 1620 (CO) | 0.78~2.55(25H, m, P(C$_6$H$_{11}$)$_2$, CCH$_2$C, H$_a$ or H$_b$ of CH$_2$P), 2.94~4.66(5H, m, H$_a$ or H$_b$ of CH$_2$P, PCH, CH$_2$NCH), 7.20~7.84(15H, m, P(C$_6$H$_5$)$_2$, C(C$_6$H$_5$)) |
| 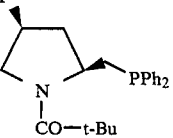 (PVCPM) | 201~203 | −5.5°(22° C.) (c 0.62, benzene) | 1617 (CO) | 0.78~2.48(25H, m, P(C$_6$H$_{11}$)$_2$, CCH$_2$C, H$_a$ or H$_b$ of CH$_2$P), 1.17(9H, s, (CH$_3$)$_3$), 2.78~3.78(2H, m, H$_a$ or H$_b$ of CH$_2$P, PCH), 3.87~4.52 (3H, m, CH$_2$NCH), 7.23~7.72(10H, m, P(C$_6$H$_5$)$_2$) |

After completion of the reaction, the solvent was removed by distillation and the resultant D-pantolactone was obtained by distillation under reduced pressure. Yield: 12.6 g (97%), $[\alpha]_D = -48.1°$ (optical yield: 94.3%)

EXAMPLE 14

Catalytic asymmetric reduction of ketopantolactone

To 50 ml of benzene were added 12.8 g (100 m-mol) of ketopantolactone, 1 mg (0.0025 m-mol) of rhodium 1,5-hexadiene chloride complex compound and 3.0 mg (0.0055 m-mol) of (2S,4S)-N-methanesulfonyl-4-dicyclohexylphosphino-2-diphenylphosphinomethylpyrrolidine (MSCPM) obtained in Example 1(h). An autoclave equipped with a stirrer, a pressure gauge and a thermometer was charged with the above mixture and a treatment was carried out in the same manner as described in Example 13 whereby 12.4 g (yield: 95%) of D-pantolactone was obtained. $[\alpha]_D = -42.1°$ (optical yield: 82.5%)

EXAMPLE 15

Catalytic asymmetric reduction of propyl pyruvate

To 50 ml of benzene were added 13.0 g (100 m-mol) of propyl pyruvate, 1 mg of rhodium 1,5-cyclooctadiene chloride complex compound and 3.1 mg (0.0055 m-mol) of (2S,4S)-N-tert-butoxy-carbonyl-4-dicyclohexylphosphino-2-diphenylphosphinomethylpyrrolidine (BCPM) obtained in Example 4. An autoclave equipped with a stirrer, a pressure gauge and a thermometer was charged with the above mixture and a treatment was carried out in the same manner as described in Example 13 whereby 12.7 g (yield: 96.2%) of propyl lactate was obtained. $[\alpha]_D = +10.5°$ (optical yield: 87%).

EXAMPLE 16

Catalytic asymmetric reduction of ethyl acetoacetate

To 3.90 g of ethyl acetoacetate were added 7.4 mg of rhodium 1,5-cyclooctadiene chloride complex compound, 22.1 mg of BCPM and 10 ml of methanol, and the mixture was charged into an autoclave. The mixture was stirred in the autoclave for 45 hours at 50° C. in hydrogen atmosphere at an initial pressure of 50 atm. It was confirmed by gas chromatography that 100% of the starting material had been converted. After distilling off the solvent, ethyl $\beta$-hydroxybutyrate was obtained almost theoretically by distillation under reduced pressure. $[\alpha]_D^{23} = -2.67°$ (neat) (optical yield: 26%).

EXAMPLE 17

Catalytic asymmetric reduction of phenacyl alcohol

To 0.68 g of phenacyl alcohol were added 12 mg of rhodium 1,5-cyclooctadiene chloride complex, 36.8 mg of BCPM and 10 ml of tetrahydrofuran. The mixture was charged into an autoclave and stirred for 45 hours at 25° C. in hydrogen atmosphere at an initial pressure of 20 atm. It was confirmed by gas chromatography that 100% of the starting material had been converted. After removing the solvent by distillation, the residue was distilled under reduced pressure whereby phenylethylene glycol was obtained almost quantitatively. $[\alpha]_D^{23} = +26.9°$ (optical yield: 66%).

EXAMPLE 18

Catalytic asymmetric reduction of phenacylamine hydrochloride

To 10 ml of methanol were added 1.20 g (7 m-mol) of phenacylamine hydrochloride, 1.7 mg (3.5×10$^{-3}$ m-mol) of rhodium 1,5-cyclooctadiene chloride complex, 5.0 mg (9.1×10$^{-3}$ m-mol) of (2S,4S)-N-phenylcarbamoyl-4-dicyclohexylphosphino-2-diphenylphosphinomethylpyrrolidine (PCCPM) and 1.8 mg ($1.8 \times 10^{-2}$ m-mol) of triethylamine, and the mixture was charged into an autoclave. The mixture was stirred in the autoclave for 20 hours at 50° C. in hydrogen atmosphere at an initial pressure of 20 atm. It was confirmed by TLC that 100% of the starting material had been converted. After concentrating the reaction mixture under reduced pressure, 10 ml of water and 0.1 g of active carbon were added to the residue and the mixture was filtered to remove insoluble matter. The filtrate was concentrated under reduced pressure until dryness, and thereafter 10 ml of benzene was added thereto. The mixture was filtered to collect crystals of the product whereby 1.11 g of 2-amino-1-phenylethanol hydrochloride was obtained. $[\alpha]_D^{23} = +40.1°$ (c=5, water) (optical yield: 82%).

EXAMPLE 19

Catalytic asymmetric reduction of N,N-diethylphenacylamine hydrochloride

In the same manner as described in Example 18, 1.59 g (7 m-mol) of N,N-diethylphenacylamine hydrochloride was reduced and subjected to the after-treatment whereby 1.49 g of N,N-diethyl-2-amino-1-phenylethanol hydrochloride was obtained. $[\alpha]_D^{23} = +57.5°$ (c=5, water)

In a similar manner, 1,47 g of the same hydrochloride was obtained by using ACPM in place of PCCPM. $[\alpha]_D^{23} = +55.9°$ (c=5, water).

EXAMPLE 20

Catalytic asymmetric reduction of pyruvoaldehyde dimethylacetal

An autoclave was charged with 1.772 g (15 m-mol) of pyruvoaldehyde dimethylacetal, 3.7 mg ($7.5 \times 10^{-3}$ m-mol) of rhodium 1,5-cyclooctadiene chloride complex, 9.4 mg ($18 \times 10^{-3}$ m-mol) of N-methoxycarbonyl-4-dicyclohexylphosphino-2-diphenylphosphinomethyl-pyrrolidine (MCPM) and 10 ml of tetrahydrofuran. The mixture was stirred in the autoclave for 48 hours at 50° C. in hydrogen atmosphere at an initial pressure of 50 atm. It was confirmed by gas chromatography that 100% of the starting material had been converted. After removing the solvent by distillation, the residue was distilled under reduced pressure whereby α-alkoxyacetal compound (b.p. 110–120° C./150 mmHg, bulb-to-bulb) was obtained at almost 100% in terms of chemical yield. $[\alpha]_D^{23} = +4.62°$ (neat). An optical yield (75%) was calculated from NMR, using Shift reagent [Eu(hfc)$_3$].

EXAMPLE 21

Catalytic asymmetric reduction of itaconic acid

To 10 ml of methanol were added 1.301 g (10 m-mol) of itaconic acid, 1.4 ml (10 m-mol) of triethylamine and 8.8 mg (0.01 m-mol) of rhodium cyclooctadiene BCPM complex perchlorate ([Rh(COD)BCPM]$^+$ClO$_4^-$). The mixture was stirred in hydrogen atmosphere at 1 atm. for 20 hours at 20° C. and the reaction mixture was concentrated under reduced pressure. To the residue was added 20 ml of an aqueous solution of 1N-NaOH and the mixture was filtered to remove insoluble matter. The filtrate was made acidic with 6N-HCl and extracted with ether. From the ethereal extract, 2-methylsuccinic acid was obtained quantitatively by distilling off the solvent. It was confirmed that the itaconic acid had been converted by 100% in view of a result of $^1$H-NMR. $[\alpha]_D^{22} = -15.51°$ (c=2.00, EtOH)(optical yield: 91.9%).

The rhodium 1,5-cyclooctadiene-BCPM complex perchlorate used in this example was prepared according to the following method:

To 0.25 g (0.8 m-mol) of rhodium 1,5-cyclooctadieneacetylacetone were added 0.087 ml (0.8 m-mol) of 60% perchloric acid and 3 ml of tetrahydrofuran,and the mixture was stirred for 10 minutes in nitrogen atmosphere. To this mixture was added a solution of 0.45 g (0.8 m-mol) of BCPMO in 1 ml of tetrahydrofuran, and the mixture was stirred for 5 minutes. Further, 15 ml of diethyl ether was added and the mixture was stirred for 30 minutes. After further addition of 15 ml of the ether, the mixture was stirred for further 30 minutes. The mixture was filtered to collect crystals whereby the complex perchlorate was obtained as yellow orange crystals in a yield of 0.50 g.

EXAMPLE 22

Catalytic asymmetric reduction of α-methyl-N-benzylideneaniline

To 10 ml of tetrahydrofuran were added 0.59 g (3 m-mol) of α-methyl-N-benzylideneaniline, 7.4 mg of rhodium 1,5-cyclooctadiene chloride complex and 22.1 mg of BCPM, and the mixture was charged into an autoclave. The mixture was stirred in the autoclave for 45 hours at 50° C. in hydrogen atmosphere at an initial pressure of 50 atm. It was confirmed that 100% of the starting material had been converted by gas chromatography. After removing the solvent by distillation, the residue was distilled under reduced pressure whereby α-methyl-N-phenylbenzylamine was obtained in almost quantitative yield. $[\alpha]_D^{23} = -5.05°$ (c=2.5, methanol) (optical yield: 28%)

EXAMPLES 23–29

Similar treatments were carried out by changing the reaction conditions, the sorts of the substrate compounds, the rhodium complex compounds, the phosphinopyrrolidine ligand compounds and solvents. Table 3 shows results of the treatments with respect to the reaction conditions, the products, the angles of rotation and the optical yields.

TABLE 3

| Example No. | Substrate compound chemical formula (Amount used) | Rhodium complex compound | Ligand | Solvent | Atm./°C./Time | Chemical formula of the Product | Angle of rotation $[\alpha]_D^{23}$ | Optical yield |
|---|---|---|---|---|---|---|---|---|
| 23 | $CH_3CCOOCH_3$<br>$\parallel$<br>$O$<br>(1.531 g) | $[Rh(COD)Cl]_2$<br>(3.7 mg) | MCCPM<br>(9.4 mg) | THF 10 ml | 20/20/24 | $CH_3CHCOOCH_3$<br>$\mid$<br>$OH$ | +7.17°<br>(neat) | 87 |
| 24 | $CH_3CCOOCH(CH_3)_2$<br>$\parallel$<br>$O$<br>(1.952 g) | $[Rh(COD)Cl]_2$<br>(3.7 mg) | MCCPM<br>(9.4 mg) | " | " | $CH_3CHCOOCH(CH_3)_2$<br>$\mid$<br>$OH$ | +8.98°<br>(neat) | 74 |
| 25 | $CH_3CCH(OCH_3)_2$<br>$\parallel$<br>$O$<br>(1.772 g) | $[Rh(COD)Cl]_2$<br>(3.7 mg) | PCPM<br>(10.5 mg) | " | 50/50/48 | $CH_3CHCH(OCH_3)_2$<br>$\mid$<br>$OH$ | +3.95°<br>(neat) | 64 |
| 26 | $C_6H_5CCH_2NH_2\cdot HCl$<br>$\parallel$<br>$O$<br>(1.20 g) | $[Rh(COD)Cl]_2$<br>(1.7 mg) | BCPM<br>(5.2 mg) | MeOH 10 ml | 20/50/20 | $C_6H_5CHCH_2NH_2\cdot HCl$<br>$\mid$<br>$OH$ | +38.8°<br>(c5, $H_2O$) | 80 |
| 27 | $C_6H_5CCH_2NHCH_3\cdot HCl$<br>$\parallel$<br>$O$<br>(1.30 g) | $[Rh(COD)Cl]_2$<br>(1.7 mg) | BCPM<br>(5.2 mg) | MeOH 10 ml<br>$Et_3N$ 1.8 mg | " | $C_6H_5CHCH_2NHCH_3\cdot HCl$<br>$\mid$<br>$OH$ | +42.4°<br>(c5, $H_2O$) | 80 |
| 28 | $C_6H_5CCH_2NCH_3(CH_2C_6H_5)\cdot HCl$<br>$\parallel$<br>$O$<br>(1.93 g) | $[Rh(COD)Cl]_2$<br>(1.7 mg) | BCPM<br>(5.2 mg) | MeOH 10 ml<br>$Et_3N$ 1.8 mg | " | $C_6H_5CHCH_2NCH_3(CH_2C_6H_5)\cdot HCl$<br>$\mid$<br>$OH$ | — | 85 |
| 29 |  | $[Rh(COD)Cl]_2$<br>(1.7 mg) | BCPM<br>(5.2 mg) | MeOH 10 ml<br>$Et_3N$ 1.8 mg | " |  | +48.9°<br>(c5, $H_2O$) | 81 |

EXAMPLE 30

Catalytic asymmetric reduction of N,N-diethylphenacylamine

In 10 ml of methanol were dissolved 1.59 g (7 m-mol) of N,N-diethylphenacylamine hydrochloride and 1.8 mg of triethylamine. To this solution were added 1.7 mg (0.0035 m-mol) of rhodium 1,5-cyclooctadiene chloride complex and 0.1 ml of a solution of 4.8 mg (0.0091 m-mol) of (2S,4S)-N-methylcarbamoyl-4-dicyclohexyl-phosphino-2-diphenylphosphinomethylpyrrolidine (MCCPM) in 10 ml of methanol.

The mixture was charged into an autoclave and stirred for 20 hours at 50° C. in hydrogen atmosphere at an initial pressure of 20atm. It was confirmed by TLC that 100% of the starting material had been converted. After concentrating the reaction mixture under reduced pressure, 10 ml of water and 0.1 g of active carbon were added to the residue and the mixture was filtered to remove insoluble matter. The filtrate was concentrated to dryness under reduced pressure, and the residue was then taken up in 10 ml of benzene, and the precipitated crystals were collected by filtration whereby 1.47 g of N,N-diethyl-2-amino-1-phenylethanol hydrochloride was obtained. $[\alpha]_D^{23} = +63.1°$ (c=5, water) (optical yield: 98% ee).

EXAMPLE 31

Catalytic asymmetric reduction of N,N-diethylphenacylamine

To 1.59 g (7 m-mol) of N,N-diethylphenacylamine hydrochloride were added 10 ml of methanol, 1.7 mg (0.0035 m-mol) of rhodium 1,5-cyclooctadiene chloride complex and 5.3 mg (0.0091 m-mol) of (2S,4S)-N-phenoxycarbonyl-4-dicyclohexylphosphino-2-iphenyl-phosphinomethylpyrrolidine (PCPM). The mixture was charged into an autoclave and stirred for 20 hours at 50° C. in hydrogen atmosphere at a pressure of 5 atm. It was confirmed by TLC that 100% of the starting material had been converted. An after-treatment was carried out in the same manner as in Example 30 whereby 1.50 g of N,N-diethyl-2-amino-1-phenylethanol hydrochloride was obtained. $[\alpha]_D^{23} = +61.1°$ (c=5, water) (optical yield: 95% ee).

It is understood that the preceding representative examples may be varied within the scope of the present specification both as to reactants and reaction conditions, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. Chiral phosphinopyrrolidine compounds of the formula:

(I)

or

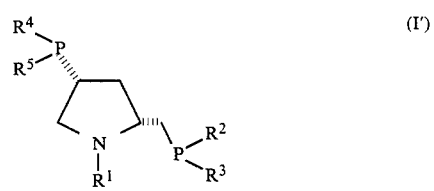

(I')

wherein $R^1$ is a hydrogen atom, —COR, —COOR, —CONHR or —SO$_2$—R where R is an alkyl or aryl group, $R^2$ and $R^3$ each represent independently, phenyl, napthyl, furyl, thienyl, pyrrolyl, pyridyl, pyrazinyl, pyrimidyl, pyridazinyl, quinolyl or isoquinolyl, which may be substituted with one or more halogen atoms, hydroxyl, alkyl or alkoxyl groups; and $R^4$ and $R^5$ represent, independently $C_1$-$C_8$ straight chain or branched chain alkyl, alkenyl or alkynyl groups which may be substituted with one or more halogen atoms, hydroxyl or alkoxy groups; and $C_5$-$C_8$ cycloalkyl, cycloalkenyl or cycloalkynyl, which may be substituted with one or more halogen atoms, hydroxyl, alkyl or alkoxy groups.

2. Chiral phosphinopyrrolidine compounds according to claim 1, wherein $R^2$ and $R^3$ each represents a phenyl group which may have a substituent or substituents and $R^4$ and $R^5$ each represents a cyclohexyl group which may have a substituent or substituents.

3. Chiral phosphinopyrrolidine compound according to claim 1, wherein $R^2$ and $R^3$ each represents a phenyl group and $R^4$ and $R^5$ each represents a cyclohexyl group.

4. The compound according to claim 1, wherein $R^4$ and $R^5$ are the same and are $C_1$-$C_8$ alkyl or $C_5$-$C_8$ cycloalkyl groups.

5. The compound according to claim 1 wherein $R^4$ and $R^5$ are the same and are $C_1$-$C_4$ alkyl, or $C_5$-$C_6$ cycloalkyl.

6. The compound according to claim 5 wherein $R^4$ and $R^5$ are cyclohexyl.

* * * * *